United States Patent
Bannae et al.

(10) Patent No.: US 12,073,937 B2
(45) Date of Patent: Aug. 27, 2024

(54) MEDICAL INFORMATION PROCESSING APPARATUS

(71) Applicant: CANON MEDICAL SYSTEMS CORPORATION, Otawara (JP)

(72) Inventors: Shuhei Bannae, Utsunomiya (JP); Maki Minakuchi, Utsunomiya (JP); Sumie Akiyama, Otawara (JP); Hisaaki Oosako, Utsunomiya (JP); Kohei Shinohara, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 391 days.

(21) Appl. No.: 17/128,883

(22) Filed: Dec. 21, 2020

(65) Prior Publication Data

US 2021/0202070 A1    Jul. 1, 2021

(30) Foreign Application Priority Data

Dec. 27, 2019 (JP) .................. 2019-238183

(51) Int. Cl.
| | | |
|---|---|---|
| *G06Q 10/00* | (2023.01) |
| *G06N 3/096* | (2023.01) |
| *G16H 30/20* | (2018.01) |
| *G16H 30/40* | (2018.01) |

(52) U.S. Cl.
CPC .............. *G16H 30/20* (2018.01); *G06N 3/096* (2023.01); *G16H 30/40* (2018.01)

(58) Field of Classification Search
CPC ......... G16H 30/20; G16H 30/40; G06N 3/096
See application file for complete search history.

(56) References Cited

U.S. PATENT DOCUMENTS

| 10,832,093 | B1* | 11/2020 | Taralova ................ G06F 18/217 |
| 10,878,090 | B2* | 12/2020 | Chistyakov ............ G06N 20/00 |
| 10,922,604 | B2* | 2/2021 | Zhao ...................... G06F 21/563 |
| 11,322,234 | B2* | 5/2022 | McNeil ................. G06F 40/242 |
| 2016/0224892 | A1 | 8/2016 | Sawada et al. |
| 2017/0153914 | A1* | 6/2017 | Rausch .................. G06F 16/245 |
| 2019/0214138 | A1* | 7/2019 | Aoyagi .................. G16H 50/70 |

(Continued)

FOREIGN PATENT DOCUMENTS

| JP | 2016-143094 A | 8/2016 |
| JP | 2019212296 A * | 12/2019 ............. G06N 20/00 |

*Primary Examiner* — Rajesh Khattar
(74) *Attorney, Agent, or Firm* — Oblon, McClelland, Maier & Neustadt, L.L.P.

(57) ABSTRACT

A medical information processing apparatus according to an embodiment includes a processing circuitry. The processing circuitry is configured: to register first relevance information relevant to a first trained model to be newly generated; to calculate, with respect to each of a plurality of second trained models being existing trained models, a similarity degree between second relevance information relevant to the second trained model and the first relevance information; to calculate a data quantity required to generate the first trained model with respect to each of the plurality of second trained models, on the basis of the similarity degrees each corresponding to a different one of the plurality of second trained models; and to output the data quantity required to generate the first trained model with respect to each of the plurality of second trained models.

9 Claims, 13 Drawing Sheets

(56) References Cited

U.S. PATENT DOCUMENTS

| | | | |
|---|---|---|---|
| 2019/0341153 A1* | 11/2019 | Ng | G16H 50/50 |
| 2020/0005088 A1* | 1/2020 | Joy | G06F 18/214 |
| 2020/0193595 A1* | 6/2020 | Iwamura | G16H 10/60 |
| 2020/0302340 A1* | 9/2020 | Durand | G06F 16/285 |
| 2020/0334567 A1* | 10/2020 | Bhattacharjee | H04L 67/125 |
| 2021/0097428 A1* | 4/2021 | Kozhaya | G06N 3/08 |
| 2021/0202070 A1* | 7/2021 | Bannae | G16H 30/40 |

* cited by examiner

| | TRAINED MODEL A | TRAINED MODEL B | TRAINED MODEL C | ... |
|---|---|---|---|---|
| DATA QUANTITY | 100 PIECES | 1,000 PIECES | 20 PIECES | ... |
| COSTS | 500,000 YEN | 5,000,000 YEN | 100,000 YEN | ... |
| TIME | 10 DAYS | 100 DAYS | 2 DAYS | ... |

FIG.8
PHANTOM IMAGE DATA OF
EXISTING MODALITY
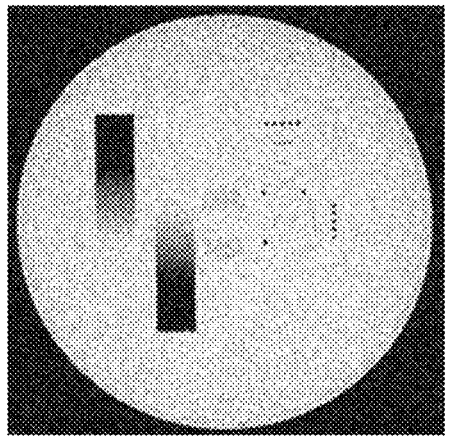
PHANTOM IMAGE DATA OF
NEW MODALITY
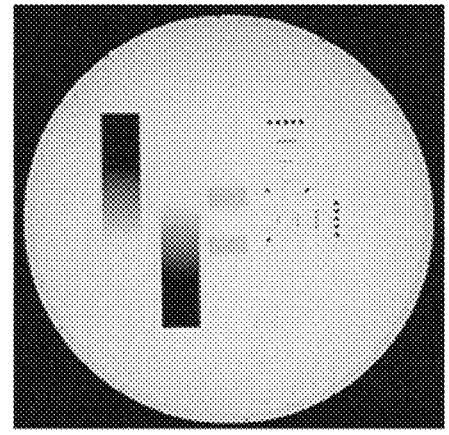

| | X-RAY CT APPARATUS | MRI APPARATUS | X-RAY ANGIOGRAPHY APPARATUS | ULTRASOUND DIAGNOSIS APPARATUS | ... |
|---|---|---|---|---|---|
| X-RAY CT APPA- RATUS | 1.0 | 0.6 | 0.4 | 0.2 | ... |
| ⋮ | ⋮ | ⋮ | ⋮ | ⋮ | ⋮ |

MEDICAL INFORMATION PROCESSING APPARATUS

CROSS-REFERENCE TO RELATED APPLICATIONS

This application is based upon and claims the benefit of priority from Japanese Patent Application No. 2019-238183, filed on Dec. 27, 2019; the entire contents of which are incorporated herein by reference.

FIELD

Embodiments described herein relate generally to a medical information processing apparatus.

BACKGROUND

Conventionally, a technique called transfer learning or the like has been disclosed by which a trained model is newly generated by performing a re-learning process on an existing trained model. By implementing such transfer learning or the like, it is possible to generate trained models having high levels of precision while using a small amount of data.

However, it is difficult to determine which one of existing trained models should be used in the re-learning process in order to achieve efficiency. For this reason, there is a demand for a technique that makes it possible to present the cost (e.g., the quantity of data required) of the re-learning process with respect to each of the existing trained models.

BRIEF DESCRIPTION OF THE DRAWINGS

FIG. 8 is a drawing illustrating examples of pieces of phantom image data between which a degree of similarity is calculated in a second embodiment;

FIG. 11 is a drawing illustrating an example of a data structure of a score table;

DETAILED DESCRIPTION

A medical information processing apparatus according to an embodiment includes a processing circuitry. The processing circuitry is configured: to register first relevance information relevant to a first trained model to be newly generated; to calculate, with respect to each of a plurality of second trained models being existing trained models, a similarity degree between second relevance information relevant to the second trained model and the first relevance information; to calculate a data quantity required to generate the first trained model with respect to each of the plurality of second trained models, on the basis of the similarity degrees each corresponding to a different one of the plurality of second trained models; and to output the data quantity required to generate the first trained model with respect to each of the plurality of second trained models.

Exemplary embodiments of a medical information processing apparatus will be explained in detail below, with reference to the accompanying drawings. Possible embodiments of the medical information processing apparatus of the present disclosure are not limited to the embodiments described below.

First Embodiment

Figure 1:
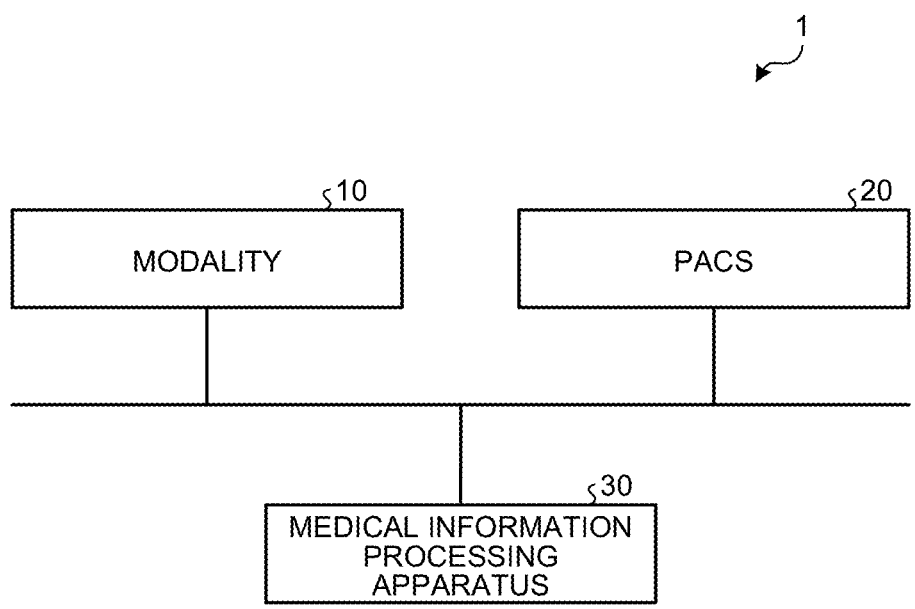
FIG. 1 is a diagram illustrating an exemplary configuration of a medical information processing system according to an embodiment.

FIG. 1 is a diagram illustrating an exemplary configuration of a medical information processing system 1 according to the present embodiment. As illustrated in FIG. 1, the medical information processing system 1 includes a modality 10, a Picture Archiving and Communication System (PACS) 20, and a medical information processing apparatus 30. Systems and apparatuses are communicably connected to one another via a network. Further, the configuration illustrated in FIG. 1 is an example, and the numbers of systems and apparatuses may arbitrarily be changed. In addition, one or more apparatuses that are not illustrated in FIG. 1 may be connected to the network.

The modality 10 is configured to generate image data of an examined subject (hereinafter "patient"). For example, the modality 10 may be a Magnetic Resonance Imaging (MRI) apparatus, an X-ray Computed Tomography (CT) apparatus, an X-ray diagnosis apparatus, an ultrasound diagnosis apparatus, a Positron Emission Tomography (PET) apparatus, or a Single Photon Emission Computed Tomography (SPECT) apparatus. Further, the modality 10 is configured to transmit the generated image data to the PACS 20.

The PACS 20 is a server apparatus configured to store therein three-dimensional information generated by the modality 10. For example, the PACS 20 is realized by using a computer device such as a server or a workstation. More specifically, the PACS 20 is configured to receive the three-dimensional information from the modality 10. Further, the PACS 20 is configured to store the three-dimensional information into a storage of its own, or the like.

The medical information processing apparatus 30 is configured to output the quantity of data (hereinafter "data quantity") required in transfer learning or the like to perform a re-learning process on an existing trained model. For example, the medical information processing apparatus 30 is realized by using a computer device such as a server or a workstation. More specifically, the medical information processing apparatus 30 is configured to calculate a degree of similarity (hereinafter, "similarity degree") between second relevance information relevant to the existing trained model and first relevance information relevant to a trained model to be newly generated. On the basis of the similarity degree, the medical information processing apparatus 30 is configured to calculate the data quantity required to generate new trained model. Further, with respect to each of existing trained models, the medical information processing apparatus 30 is configured to output the data quantity required to generate the new trained model.

Next, a configuration of the medical information processing apparatus 30 according to the present embodiment will be explained.

Figure 2:
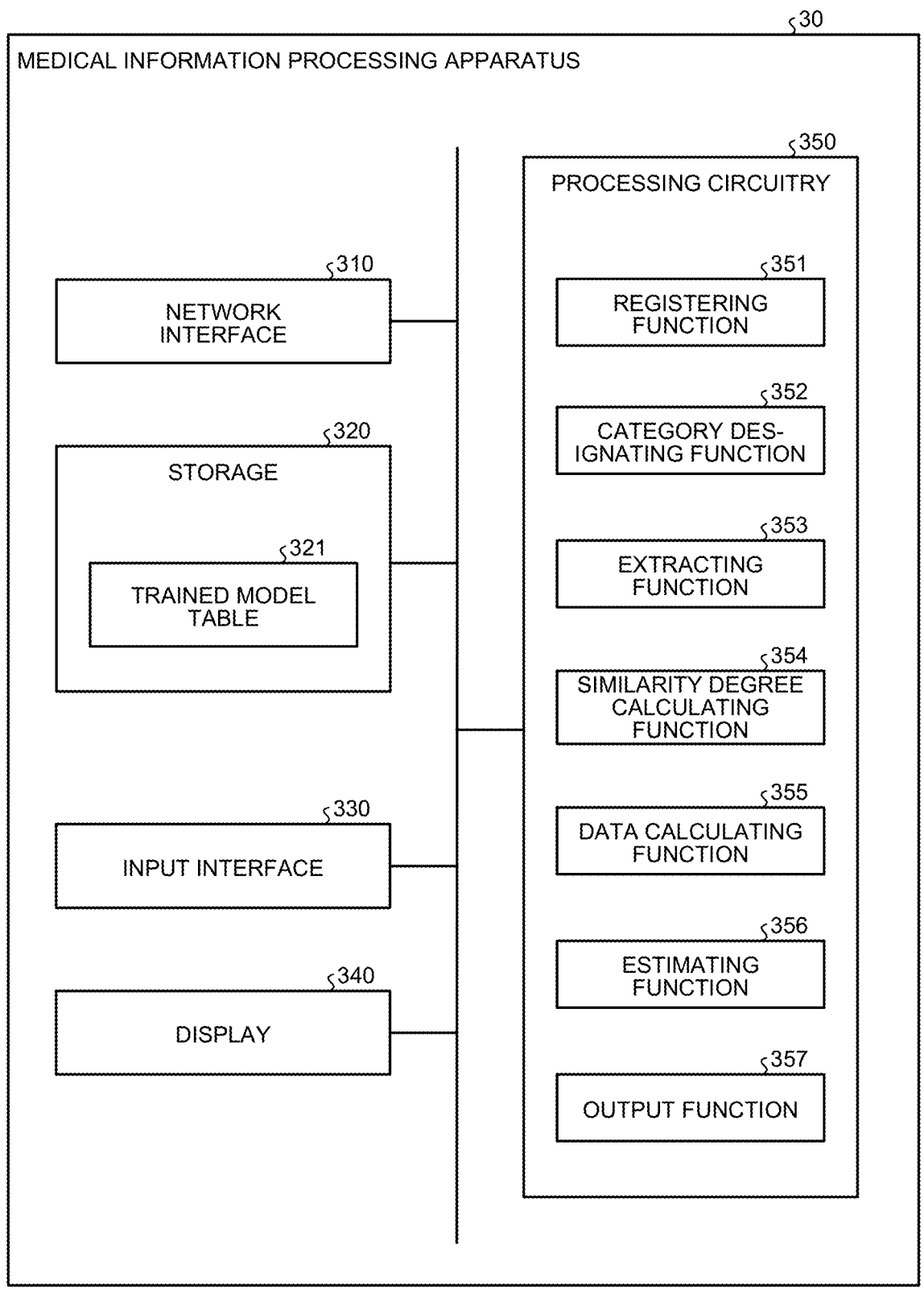
FIG. 2 is a block diagram illustrating an exemplary configuration of a medical information processing apparatus according to the present embodiment.

FIG. 2 is a block diagram illustrating the exemplary configuration of the medical information processing apparatus 30 according to the present embodiment. As illustrated in FIG. 2, the medical information processing apparatus 30 according to the present embodiment includes a network interface 310, a storage 320, an input interface 330, a display 340, and a processing circuitry 350.

The network interface 310 is connected to the processing circuitry 350 and is configured to control transfer of various types of data and communication that are performed via a network with the modality 10 and the PACS 20. More specifically, the network interface 310 is configured to receive various types of information from the systems and to output the received information to the processing circuitry 350. For example, the network interface 310 is realized by using a network card, a network adaptor, a Network Interface Controller (NIC), or the like.

The storage 320 is connected to the processing circuitry 350 and is configured to store various types of data therein. For example, the storage 320 is realized by using a semiconductor memory element such as a Random Access Memory (RAM) or a flash memory, or a hard disk, an optical disk, or the like.

Figure 3:
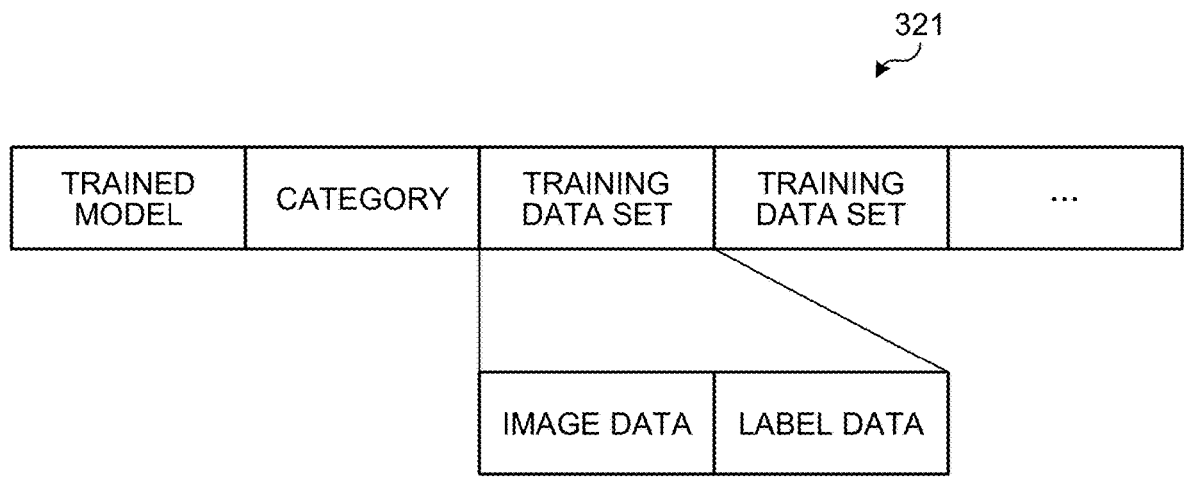
FIG. 3 is a drawing illustrating an example of a data structure of a trained model table.

The storage 320 is configured to store therein a trained model table 321. FIG. 3 is a drawing illustrating an example of a data structure of the trained model table 321. The trained model table 321 is trained model information keeping a trained model, a category thereof, and a plurality of training data sets in correspondence with one another. The trained model is an existing trained model. The category is information indicating a category in deep learning with respect to the existing trained model kept in correspondence therewith. Examples of the category include image classification, image detection, and image segmentation. The image classification is identifying included objects of the image. The image detection is identifying included objects of the image and identifying where in the image the identified objects are positioned. The image segmentation is identifying objects included in the image in units of pixels.

The training data sets is data that was used in a learning process of the existing trained model kept in correspondence therewith. The training data sets each include training data and label data. The training data is the data that was used in a learning process of the existing trained model. For example, the training data is image data generated by the modality 10 or the like. The training data does not necessarily have to be image data and may be data in another format. The label data is information for identifying objects included in the training data. When the category is the image classification, the label data is information indicating the included objects of the image. When the category is the image detection, the label data includes information indicating the included objects of the image and information about coordinates or the like indicating the positions of the objects. When the category is the image segmentation, the label data is information indicating the included objects of the image in units of pixels. In the present embodiment, an example will be explained in which the training data sets each include the training data and the label data. However, the training data sets do not necessarily have to include the label data.

The input interface 330 is configured to convert an input operation received from a user into an electrical signal and to output the electrical signal to the processing circuitry 350. For example, the input interface 330 is realized by a using one or more input devices such as a trackball, a switch button, a mouse, a keyboard, a touchpad on which input operations are performed by touching an operation surface thereof, a touch screen in which a display screen and a touchpad are integrally formed, a contactless input interface using an optical sensor, an audio input interface, and/or the like. In an example, the input interface 330 may be a controlling circuitry for a connection interface or the like configured to receive electronic signals corresponding to operations from an operation device provided separately from the medical information processing apparatus 30.

The display 340 is configured to display various types of information and various types of images output from the processing circuitry 350. For example, the display 340 is realized by using a display such as an organic Electro Luminescence (EL) monitor, a liquid crystal monitor, a Cathode Ray Tube (CRT) monitor, or a touch panel. For example, the display 340 is configured to display a Graphical User Interface (GUI) used for receiving instructions from the user, various types of display-purpose image data, and various types of processing results obtained by the processing circuitry 350.

The processing circuitry 350 is configured to control constituent elements of the medical information processing apparatus 30. For example, the processing circuitry 350 is realized by using a processor. More specifically, the processing circuitry 350 according to the present embodiment includes a registering function 351, a category designating function 352, an extracting function 353, a similarity degree calculating function 354, a data calculating function 355, an estimating function 356, and an output function 357.

In this situation, for example, processing functions performed by the constituent elements of the processing circuitry 350 illustrated in FIG. 2, namely, the registering function 351, the category designating function 352, the extracting function 353, the similarity degree calculating function 354, the data calculating function 355, the estimating function 356, and the output function 357, are stored in the storage 320 in the form of computer-executable programs. The processing circuitry 350 is a processor configured to realize the functions corresponding to the programs, by reading and executing the programs from the storage 320. In other words, the processing circuitry 350 that has read the programs has the functions illustrated within the processing circuitry 350 in FIG. 2.

Alternatively, all the processing functions, namely, the registering function 351, the category designating function 352, the extracting function 353, the similarity degree calculating function 354, the data calculating function 355, the estimating function 356, and the output function 357, may be recorded in the storage 320 in the form of a single computer-executable program. For example, this program may be referred to as a medical information processing program. In that situation, the processing circuitry 350 realizes the registering function 351, the category designating function 352, the extracting function 353, the similarity degree calculating function 354, the data calculating function 355, the estimating function 356, and the output function 357 corresponding to the medical information processing program, by reading the medical information processing program from the storage 320 and executing the read medical information processing program.

The registering function 351 is an example of a registering unit. The registering function 351 is configured to register first relevance information relevant to a first trained model that is a trained model to be newly generated. The first relevance information is image data used by the trained model to be newly generated in a learning process. Alternatively, the registering function 351 may register the first relevance information including first label data that is label data indicating information for identifying the first relevance information. More specifically, the first label data is used for determining which category of deep learning corresponds to the first trained model relevant to the first relevance information. In other words, the first label data is used for determining which one of the image classification, the image detection, and the image segmentation is applicable. Further, when a plurality of pieces of first relevance information are present, the registering function 351 may register a representative piece of first relevance information selected from among the plurality of pieces of first relevance information, may register one piece of first relevance information obtained by integrating together the plurality of pieces of first relevance information, may register an average piece of first relevance information among the plurality of pieces of first relevance information, or may register the plurality of pieces of first relevance information.

The category designating function 352 is an example of a designating unit. The category designating function 352 is configured to designate the category in deep learning, with respect to the trained model to be newly generated. For example, the category designating function 352 is configured to designate one of the image classification, the image detection, and the image segmentation. For example, the category designating function 352 is configured to designate the category specified by an operation.

Alternatively, the category designating function 352 is configured to designate the category on the basis of the first label data, when the registering function 351 has registered the first relevance information including the first label data. In other words, the category designating function 352 designates the image classification when the first label data corresponds to the image classification, designates the image detection when the first label data corresponds to the image detection, and designates the image segmentation when the first label data corresponds to the image segmentation.

The extracting function 353 is an example of a first extracting unit. The extracting function 353 is configured to extract one or more second trained models that belong to the category designated by the category designating function 352, from trained model information keeping the following in correspondence with one another: second trained models that are existing trained models; categories of the second trained models in deep learning; and second relevance information relevant to the second trained models. The second trained models are the existing trained models stored in the trained model table 321. The second relevance information is image data that was used in the learning processes of the existing trained models. Further, the second relevance information may include label data. In other words, the extracting function 353 is configured to extract the one or more trained models belonging to the category designated by the category designating function 352, from the trained model table 321.

The similarity degree calculating function 354 is an example of a first calculating unit. The similarity degree calculating function 354 is configured to calculate, with respect to each of the plurality of second trained models, a similarity degree between the second relevance information relevant to the existing trained model and the first relevance information. Further, the similarity degree calculating function 354 is configured to calculate a similarity degree with respect to each of the one or more existing trained models extracted by the extracting function 353. More specifically, the similarity degree calculating function 354 calculates the similarity degree between the second relevance information of each of the one or more existing trained models extracted by the extracting function 353 from the existing trained models stored in the trained model table 321 and the first relevance information of the trained model to be newly generated.

The similarity degree calculating function 354 is configured to calculate the similarity degree by implementing a method such as a Mean Square Error (MSE) method or a Structural Similarity (SSIM) method, on average pixel values, a histogram scheme, correlational coefficients, frequency components, or the like. In this situation, when there are two or more pieces of second relevance information or first relevance information, the similarity degree calculating function 354 calculates a plurality of similarity degrees with respect to each of the existing trained models. Further, the similarity degree calculating function 354 calculates the similarity degree with respect to each of the existing trained models, by using a value obtained through a statistical method such as an average value or a median value.

Alternatively, the similarity degree calculating function 354 may calculate the similarity degree on the basis of the first label data of the first relevance information and second label data which is label data being information for identifying the second relevance information. The second label data is used for determining which category of deep learning corresponds to the second trained model relevant to the second relevance information. In other words, the second label data is used for determining which one of the image classification, the image detection, and the image segmentation is applicable. It means that the similarity degree calculating function 354 may calculate the similarity degree by taking into account the first label data of the first relevance information and the second label data of the second relevance information. When the category is the image segmentation, what is learned changes depending on the position, size, shape, range, and/or the like of the objects included in the label data. Accordingly, the similarity degree calculating function 354 is able to improve the precision level of the similarity degree by adding label data of the similarity degree.

Figure 4:
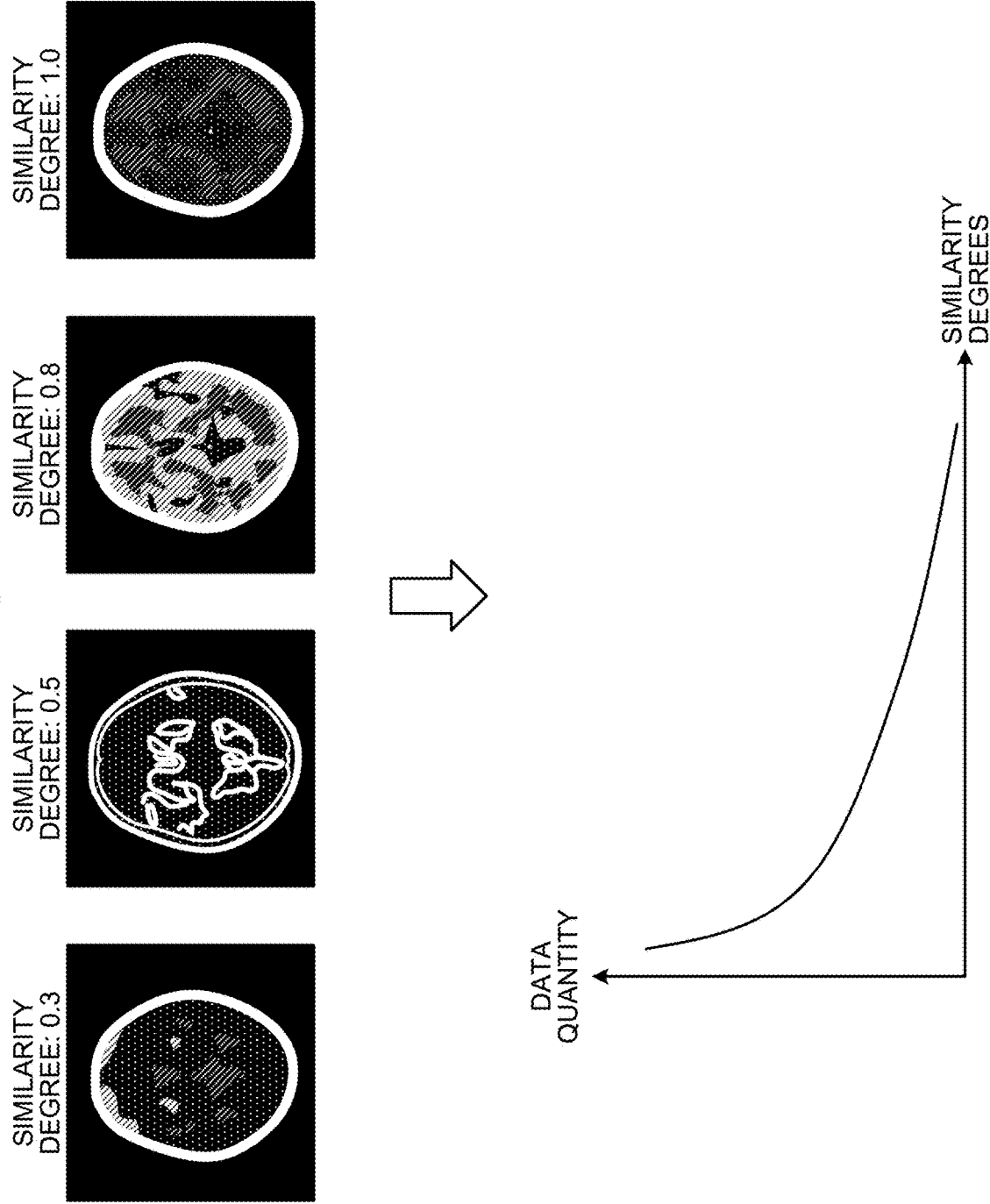
FIG. 4 is a drawing illustrating an example of a data quantity calculation method.

The data calculating function 355 is an example of a second calculating unit. On the basis of the similarity degrees each corresponding to a different one of the plurality of existing trained models, the data calculating function 355 is configured to calculate the data quantity required to generate the new trained model with respect to each of the plurality of existing trained models. FIG. 4 is a drawing illustrating an example of a data quantity calculation method. At first, with respect to the image data that was used in the learning process of each existing trained model, a plurality of pieces of image data having mutually-different similarity degrees are prepared. By calculating backwards from the similarity degrees, the data calculating function 355 generates the pieces of image data having the mutually-different similarity degrees. For example, the data calculating function 355 generates the pieces of image data having the mutually-different similarity degrees, by performing an image processing process to emphasize the edge of a tissue shape or an object. It is also acceptable to generate the pieces of image data having the mutually-different similarity degrees by using other image processing processes, instead of the image processing process to emphasize the edge. It is also acceptable to prepare the pieces of image data having the mutually-different similarity degrees by using other methods besides image processing. In the example of FIG. 4, pieces of image data having a similarity degree of 1.0, a similarity degree of 0.8, a similarity degree of 0.5, and a similarity degree of 0.3 are prepared.

The data calculating function 355 is configured to calculate the data quantity required to generate the new trained model, with respect to each of the similarity degrees. More specifically, the data calculating function 355 is configured to perform a learning process by using image data corresponding to each of the similarity degrees. Accordingly, the data calculating function 355 derives a data quantity required to achieve each of various precision levels when the learning process is performed by using the image data of a certain similarity degree. Further, the data calculating function 355 is configured to generate a graph indicating a relationship between required data quantities and similarity degrees, with respect to each of the existing trained models.

In this situation, the similarity degree calculating function 354 is configured to calculate the similarity degree with respect to each of the existing trained models. Accordingly, the data calculating function 355 is able to calculate the data quantity required to generate the new trained model with respect to each of the existing trained models, by extracting, from the graph, a required data quantity corresponding to the similarity degree calculated by the similarity degree calculating function 354.

The estimating function 356 is an example of an estimating unit. The estimating function 356 is configured to estimate a correlational relationship between the data quantities required to generate the new trained model and precision levels of output results to be output by the newly-generated trained model. In this situation, the precision levels denote accuracy rates of the output results from the trained model. Further, the estimating function 356 is configured to generate a graph indicating the correlational relationship between the data quantities required to generate the new trained model and the precision levels, with respect to each of the existing trained models.

Figures 5, 6:
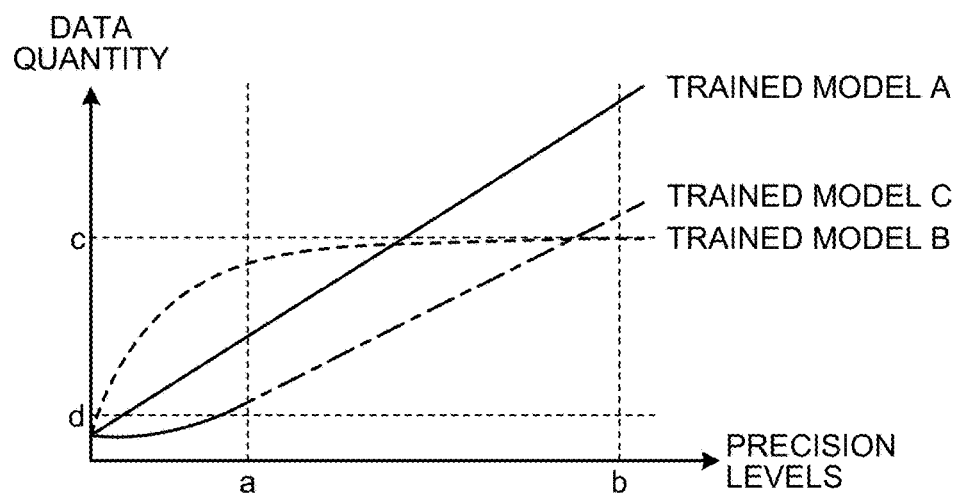
FIG. 5 is a table illustrating an example of a list of required quantities.
FIG. 6 is a chart illustrating an example of a graph indicating correlational relationships.

The output function 357 is an example of an output unit. The output function 357 is configured to output the data quantity required to generate the new trained model, with respect to each of the plurality of existing trained models. In other words, the output function 357 is configured to output the data quantity required to generate the new trained model that was calculated by the data calculating function 355. The output function 357 is configured to output a list of required quantities being required to generate the new trained model. FIG. 5 is a table illustrating an example of the list of required quantities. As illustrated in FIG. 5, the output function 357 displays the list indicating a data quantity, costs, and a time period required to generate the new trained model, with respect to each of the existing trained models. The data quantities are each the data quantity calculated by the data calculating function 355. The costs each indicate an amount of money required to obtain the data in the data quantity. For example, the costs are calculated on the basis of a cost to purchase unit data, a labor cost to create the unit data, and the like. The time periods each indicate a time period required to obtain the data in the data quantity. For example, the costs are each calculated on the basis of the time period required to create the unit data or the like.

The output function 357 is configured to output information indicating the correlational relationships estimated by the estimating function 356, by using a graph or the like. FIG. 6 is a chart illustrating an example of the graph indicating the correlational relationships. As illustrated in FIG. 6, the output function 357 displays the graph indicating the correlational relationship between the data quantities and the precision levels with respect to an existing trained model A, an existing trained model B, and an existing trained model C. As a result of having the graph displayed in this manner, the user is able to select a trained model suitable for his/her situation.

For example, when it is known that the precision level "a" indicated in FIG. 6 is necessary, the user is able to adopt the trained model C having the smallest data quantity for "a". In another example, when it is known that the precision level "b" indicated in FIG. 6 is necessary, the user is able to adopt the trained model B having the smallest data quantity for "b". In yet another example, when it is known that it is possible to prepare data in the data quantity "c" indicated in FIG. 6, the user is able to adopt the trained model B having the highest precision level for "c". In yet another example, when it is known that it is possible to prepare data only in the data quantity "d" indicated in FIG. 6, the user is able to adopt the trained model C having the highest precision level for "d".

Figure 7:
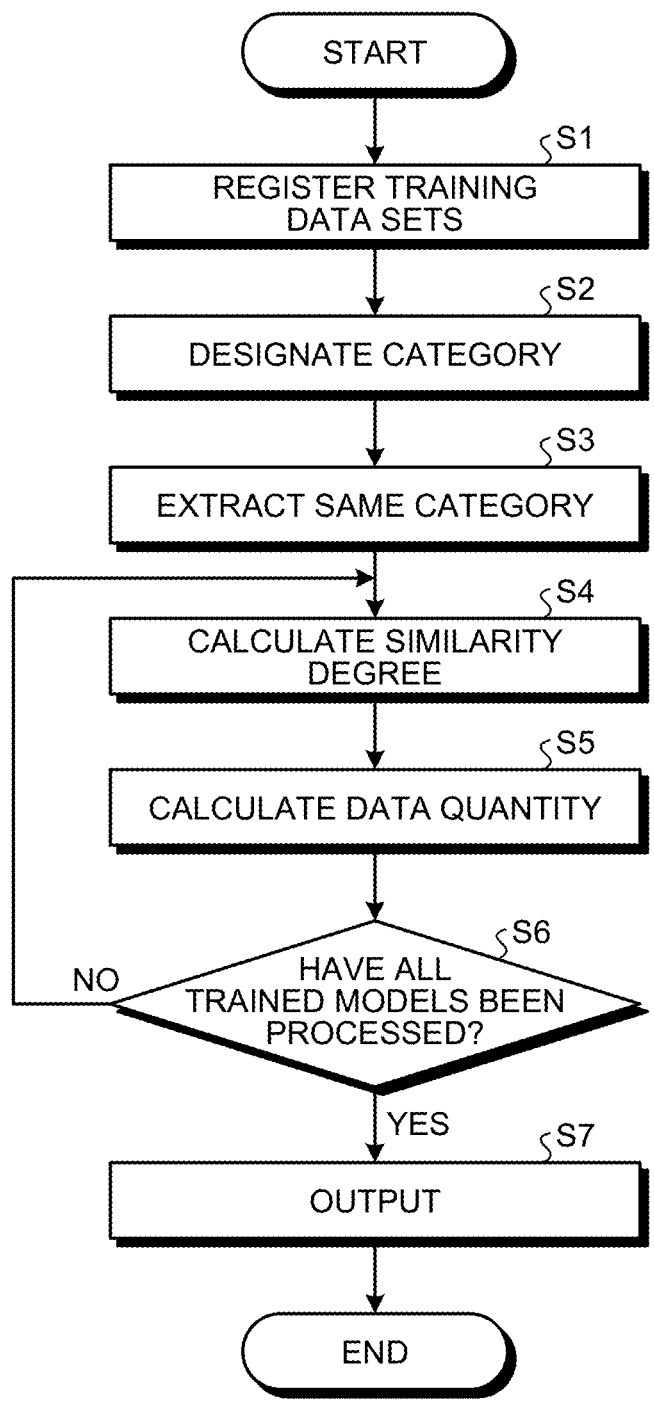
FIG. 7 is a flowchart illustrating a processing procedure in an output process performed by the medical information processing apparatus according to the present embodiment.

Next, an output process performed by the medical information processing apparatus 30 according to the present embodiment will be explained. The output process is a process to output the data quantity required to generate the new trained model. FIG. 7 is a flowchart illustrating a processing procedure in the output process performed by the medical information processing apparatus 30 according to the present embodiment.

The registering function 351 registers the training data sets used in the learning process of the trained model to be newly generated (step S1).

The category designating function 352 designates a category of the trained model to be newly generated (step S2).

The extracting function 353 extracts a trained model belonging to the same category as the category designated by the category designating function 352, from the trained model table 321 (step S3).

The similarity degree calculating function 354 calculates a similarity degree between the training data sets of the trained model extracted by the extracting function 353 and the training data sets of the trained model to be newly generated (step S4).

On the basis of the similarity degree calculated by the similarity degree calculating function 354, the data calculating function 355 calculates a data quantity required to generate the newly-generated trained model (step S5).

The similarity degree calculating function 354 judges whether or not a similarity degree has been calculated with respect to the training data sets of all the trained models extracted by the extracting function 353 (step S6). When the similarity degree has not been calculated with respect to the training data sets of all the trained models (step S6: No), the similarity degree calculating function 354 proceeds to step S4 to calculate a similarity degree with respect to the training data sets of the one or more trained models of which the similarity degree has not yet been calculated.

When a similarity degree has been calculated with respect to the training data sets of each of all the trained models (step S6: Yes), the output function 357 outputs the data quantity required to generate the new trained model that was calculated by the data calculating function 355, with respect to each of the existing trained models (step S7).

The medical information processing apparatus 30 thus ends the output process.

As explained above, the medical information processing apparatus 30 according to the first embodiment is configured to calculate the similarity degree between the image data used for the trained model to be newly generated and the image data that was used for generating each of the existing trained models. Further, the medical information processing apparatus 30 is configured to output the data quantity required to generate the new trained model corresponding to the calculated similarity degree, with respect to each of the existing trained models. Accordingly, the medical information processing apparatus 30 is able to output the data quantities required in the re-learning process. In this manner, the medical information processing apparatus 30 is configured to output the data quantity required to generate the new trained model, with respect to each of the plurality of existing trained models. Accordingly, the user is able to estimate the costs such as the data quantity required in the learning process. Consequently, the user is able to determine which trained model is more efficient to be used as the existing trained model serving as a basis of the trained model to be newly generated through the re-learning process.

Second Embodiment

Next, a medical information processing apparatus 30a (see FIG. 9) according to a second embodiment will be explained. Some of the constituent elements that are the same as those in the first embodiment described above will be referred to by using the same reference characters, and the explanations thereof will be omitted.

The second embodiment is based on a situation where a trained model is generated with respect to each modality 10. When a modality 10 has newly been introduced, it is necessary to generate a trained model adaptive to the newly-introduced modality 10. Thus, the trained model adaptive to the newly-introduced modality 10 is generated by performing a re-learning process (e.g., transfer learning) on a trained model of an existing modality 10.

In the first embodiment, the similarity degree is calculated between the image data that was used in the learning process of each of the existing trained models and the image data used in the learning process of the trained model to be newly generated. In contrast, the second embodiment is based on the situation where a trained model adaptive to the newly-introduced modality 10 is to be generated. For this reason, there may be some situations where it is not possible to prepare the image data used for calculating the similarity degree, unlike in the first embodiment. Accordingly, in the second embodiment, a similarity degree is calculated between phantom image data of the existing modality 10 and phantom image data of the new modality 10. Further, the first relevance information in the second embodiment is phantom image data of the new modality 10. In contrast, the second relevance information is phantom image data of the existing modality 10.

FIG. 8 is a drawing illustrating examples of pieces of phantom image data between which a similarity degree is calculated in the second embodiment. Each of the pieces of phantom image data is image data used for evaluating capabilities of apparatuses and is generated by imaging an object called a phantom used for a capability evaluation purpose. Further, the existing modality 10 and the new modality 10 each generate the phantom image data by imaging the phantom under mutually the same image taking conditions. With these arrangements, in the second embodiment, a similarity degree between the capabilities of the modalities 10 is recognized. Further, in the second embodiment, a data quantity required in the re-learning process is calculated on the basis of the similarity degree between the capabilities of the modalities 10.

Figure 9:
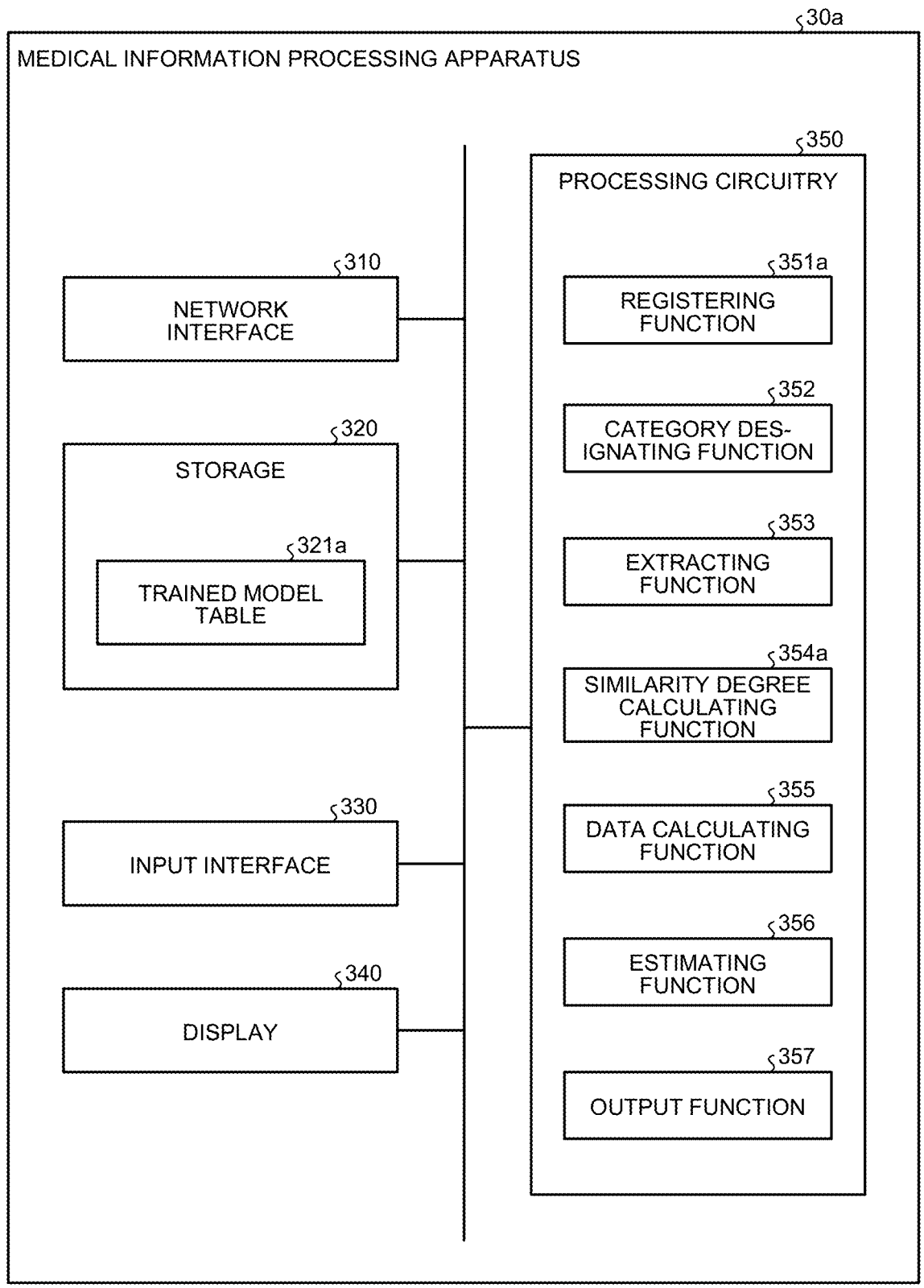
FIG. 9 is a block diagram illustrating an exemplary configuration of a medical information processing apparatus according to the second embodiment.

FIG. 9 is a block diagram illustrating an exemplary configuration of a medical information processing apparatus 30a according to the second embodiment.

A trained model table 321a keeps the following in correspondence with one another: trained models; the categories of the trained models in deep learning; a plurality of training data sets; and phantom image data taken under the same image taking conditions as those of the image data included in the training data sets.

A registering function 351a is configured to register the phantom image data as the first relevance information relevant to the trained model to be newly generated. More specifically, the registering function 351a is configured to register the phantom image data taken by the newly-introduced modality 10 under the same image taking conditions as those of the phantom image data stored in the trained model table 321a.

A similarity degree calculating function 354a is configured to calculate the similarity degree between the phantom image data of the modality 10 that generates the image data used for generating the newly-generated trained model and the phantom image data of the modality 10 that generated the image data that was used for generating each existing trained model. More specifically, the similarity degree calculating function 354a is configured to calculate the similarity degree between the phantom image data stored in the trained model table 321a and the phantom image data registered by the registering function 351a.

On the basis of the similarity degrees each corresponding to a different one of the existing trained models, the data calculating function 355 is configured to calculate a data quantity required to generate the new trained model with respect to each of the existing trained models.

The output function 357 is configured to output the data quantity required in the generation, with respect to each of the second trained models.

As explained above, the medical information processing apparatus 30a according to the second embodiment is configured to calculate the similarity degree between the phantom image data taken under the same image taking conditions as those of the image data that was used for generating each of the existing trained models and the phantom image data used for generating the newly-generated trained model. Further, the medical information processing apparatus 30a is configured to output the data quantity required to generate the new trained model corresponding to the calculated similarity degree, with respect to each of the existing trained models. Consequently, the medical information processing apparatus 30a according to the second embodiment is able to output the data quantity required to generate the new trained model with respect to each of the existing trained models, even when it is not possible to prepare the image data taken of the examined subject (e.g., the patient).

Third Embodiment

Next, a medical information processing apparatus 30b (see FIG. 10) according to a third embodiment will be explained. Some of the constituent elements that are the same as those in the first embodiment described above will be referred to by using the same reference characters, and the explanations thereof will be omitted.

In the second embodiment, to generate the trained model adaptive to the newly-introduced modality 10, the similarity degree is calculated between the phantom image data of the existing modality 10 and the phantom image data of the new modality 10. In the third embodiment, a similarity degree is calculated between obtaining conditions of image data. For example, the obtaining conditions include items such as the type of the modality 10, as well as the manufacturer, the model, the version, image taking methods, and/or reconstruction conditions of the modality 10. The obtaining conditions may include other items.

Figure 10:
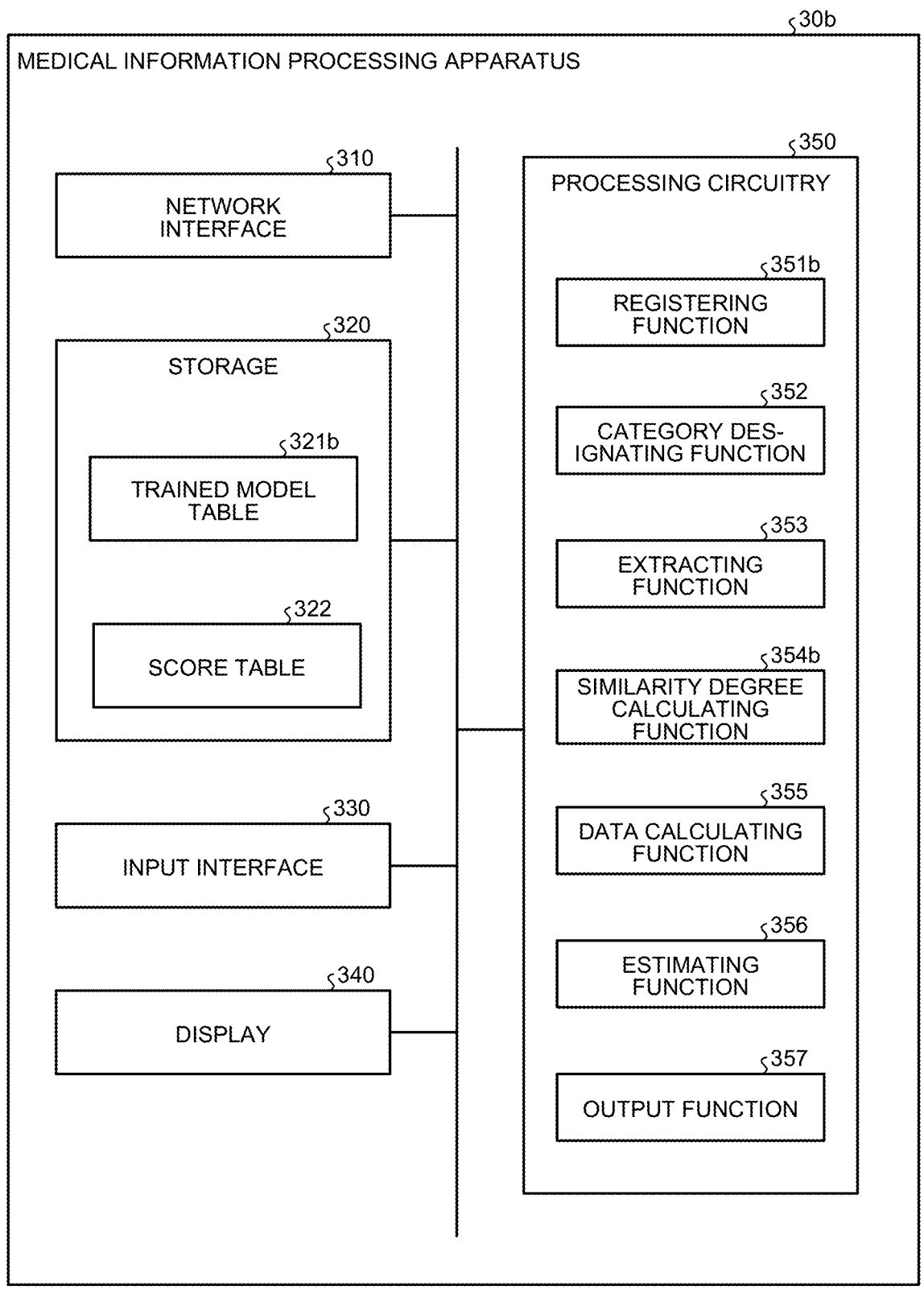
FIG. 10 is a block diagram illustrating an exemplary configuration of a medical information processing apparatus according to a third embodiment.

FIG. 10 is a block diagram illustrating an exemplary configuration of the medical information processing apparatus 30b according to the third embodiment.

A trained model table 321b according to the third embodiment keeps the following in correspondence with one another: trained models; the categories thereof; a plurality of training data sets; and obtaining conditions of the image data included in the training data sets.

Further, the storage 320 has a score table 322 stored therein. FIG. 11 is a drawing illustrating an example of a data structure of the score table 322. The score table 322 includes a score of each of the items of the obtaining conditions. The score table 322 in FIG. 11 indicates scores corresponding to types of the modality 10, which is an item of the obtaining conditions. When the type of the modality 10 is an X-ray CT apparatus, the score is 1.0 if the type of another modality 10 indicated in the obtaining conditions to be compared is an X-ray CT apparatus; the score is 0.6 for an MRI apparatus; the score is 0.4 for an X-ray angiography apparatus; and the score is 0.2 for an ultrasound diagnosis apparatus. Further, although the score table 322 in FIG. 11 indicates the scores corresponding to the different types of modalities 10, the score table 322 similarly has scores for the other items included in the items of the obtaining conditions. Further, the first relevance information in the third embodiment is the obtaining conditions of the image data used in the learning process of the trained model to be newly generated. Further, the second relevance information is the obtaining conditions of the image data that was used in the learning process of each of the existing trained models.

A registering function 351b is configured to register the obtaining conditions as the first relevance information relevant to the first trained model to be newly generated. In other words, the registering function 351b is configured to register the obtaining conditions of the image data used in the learning process of the trained model to be newly generated.

A similarity degree calculating function 354b is configured to calculate a similarity degree between the first relevance information indicating the obtaining conditions of the image data used for generating the newly-generated trained model and the second relevance information indicating the obtaining conditions of the image data that was used for generating each of the existing trained models. More specifically, on the basis of the score table 322, the similarity degree calculating function 354b is configured to extract the scores of the items of the obtaining conditions stored in the trained model table 321b and of the items of the obtaining conditions registered by the registering function 351b. Further, the similarity degree calculating function 354b is configured to calculate similarity degrees on the basis of the scores of the items. The similarity degree calculating function 354b is configured to calculate a similarity degree in this manner with respect to each of the existing trained models.

On the basis of the similarity degrees each corresponding to a different one of the existing trained models, the data calculating function 355 is configured to calculate a data quantity required to generate the new trained model, with respect to each of the existing trained models.

The output function 357 is configured to output the data quantity required in the generation, with respect to each of the second trained models.

As explained above, the medical information processing apparatus 30b according to the third embodiment is configured to calculate the similarity degree between the obtaining conditions of the image data that was used for generating each of the existing trained models and the obtaining conditions of the image data used for generating the newly-generated trained model. Further, the medical information processing apparatus 30b is configured to output the data quantity required to generate the new trained model corresponding to the calculated similarity degree, with respect to each of the existing trained models. Consequently, the medical information processing apparatus 30b according to the third embodiment is able to output the data quantity required to generate the new trained model with respect to each of the existing trained models, even when it is not possible to prepare the image data taken of the examined subject (e.g., the patient).

Fourth Embodiment

Next, a medical information processing apparatus 30c (see FIG. 12) according to a fourth embodiment will be explained. Some of the constituent elements that are the same as those in the first embodiment described above will be referred to by using the same reference characters, and the explanations thereof will be omitted.

The medical information processing apparatus 30c according to the fourth embodiment is configured to calculate the balance (a remaining amount) to reach the data quantity required to generate the newly-generated trained model.

Figure 12:
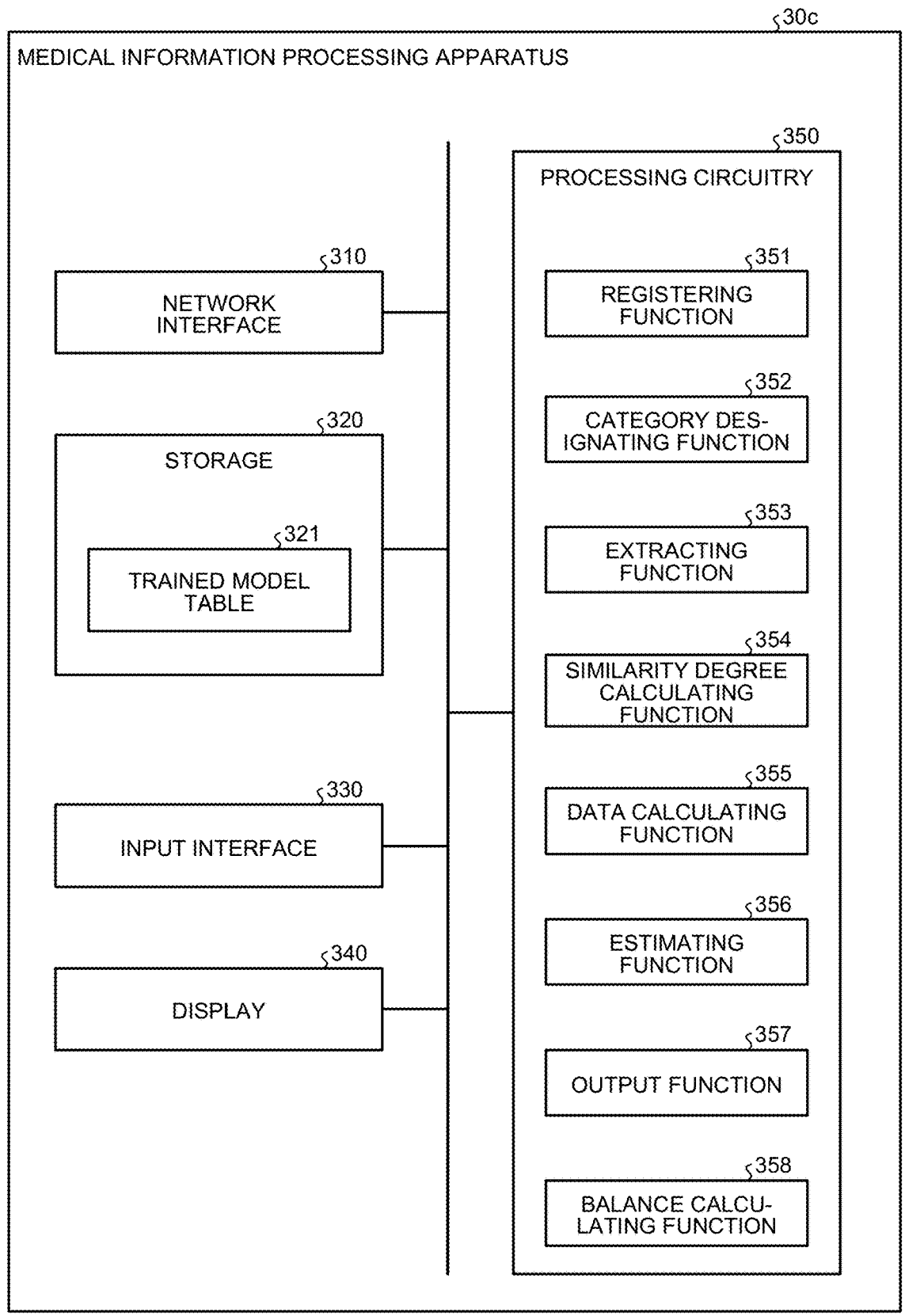
FIG. 12 is a block diagram illustrating an exemplary configuration of a medical information processing apparatus according to a fourth embodiment.

FIG. 12 is a block diagram illustrating an exemplary configuration of the medical information processing apparatus 30c according to the fourth embodiment.

The medical information processing apparatus 30c according to the fourth embodiment includes a balance calculating function 358 configured to calculate the balance to reach the data quantity required to generate the newly-generated trained model. The balance calculating function 358 is an example of a third calculating unit. The balance calculating function 358 is configured to calculate the data quantity required to achieve a precision level serving as a target value, on the basis of an estimation result estimated by the estimating function 356. More specifically, the balance calculating function 358 receives, from the trained model table 321, a designation of an existing trained model for which the balance is to be calculated and a designation of the target value. In this situation, the estimating function 356 is configured to estimate a correlational relationship between data quantities and precision levels. Accordingly, on the basis of the estimation result obtained by the estimating function 356, the balance calculating function 358 calculates the data quantity that needs to be re-learned, before generating the trained model having the precision level serving as the target value, from the designated trained model.

Further, the data quantity varies depending on the similarity degree. Accordingly, with respect to the designated trained model, the balance calculating function 358 calculates, with respect to each similarity degree, a data quantity required to achieve the precision level serving as the target value from the current precision level. Further, on the basis of the estimation result obtained by the estimating function 356, the balance calculating function 358 generates a graph indicating, with respect to each similarity degree, the data quantity that needs to be re-learned before generating the trained model having the precision level serving as the target value from the designated trained model.

Figure 13:
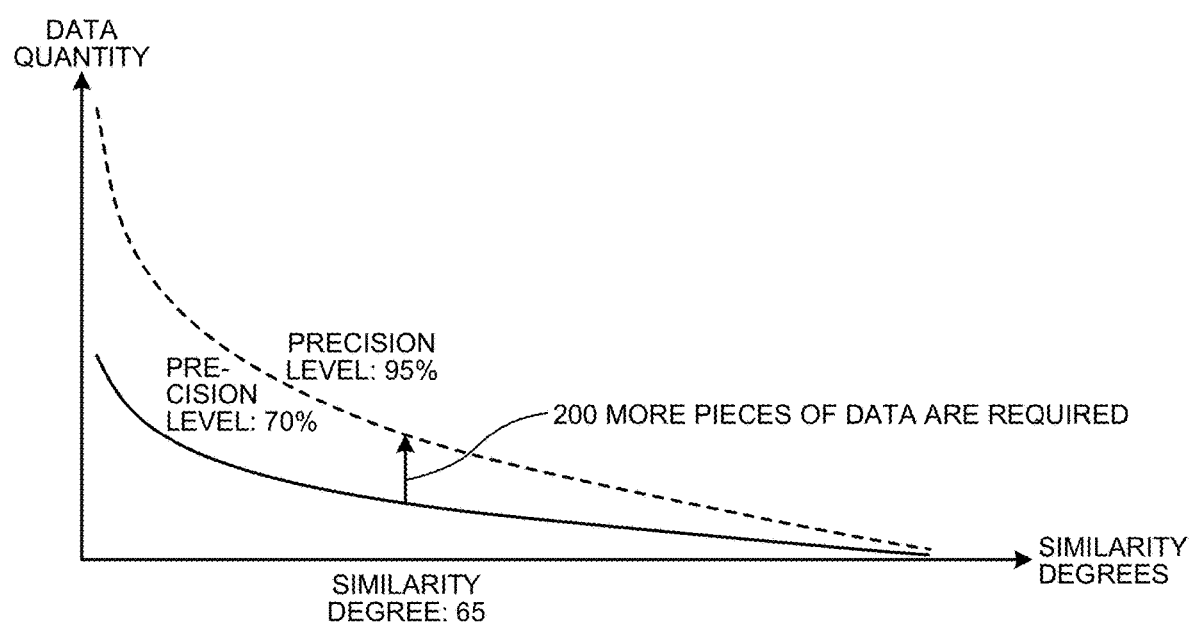
FIG. 13 is a chart illustrating an example of a graph indicating a correlational relationship between data quantities and degrees of similarity for each of different precision levels.

The output function 357 is configured to output the data quantity calculated by the balance calculating function 358. Further, the output function 357 is configured to output the graph generated by the balance calculating function 358. FIG. 13 is a chart illustrating an example of the graph indicating a correlational relationship between data quantities and similarity degrees with respect to each of the different precision levels. As illustrated in FIG. 13, for each of the designated trained models and with respect to each of the precision levels, the graph indicates the correlational relationship between data quantities and similarity degree. Further, the graph indicates how many more pieces of data are required for a specific similarity degree to achieve the precision level designated by the estimating function 356.

As explained above, the medical information processing apparatus 30c according to the fourth embodiment is configured to output the data quantity required to achieve the precision level serving as the target value, on the basis of the estimation result estimated by the estimating function 356. Accordingly, the user is able to understand how many more pieces of data need to be prepared.

Fifth Embodiment

Next, a medical information processing apparatus 30d (see FIG. 14) according to a fifth embodiment will be explained. Some of the constituent elements that are the same as those in the first embodiment described above will be referred to by using the same reference characters, and the explanations thereof will be omitted.

The medical information processing apparatus 30d according to the fifth embodiment is configured to output an item of the obtaining conditions that will improve a precision level. The precision level is expected to be improved by improving the similarity degrees of the obtaining conditions. Accordingly, the medical information processing apparatus 30d is configured to extract the item reducing the similarity degree, between the obtaining conditions of the image data used for generating the newly-generated trained model and the obtaining conditions of the image data that was used for generating an existing trained model. With this arrangement, the medical information processing apparatus 30d is configured to output the item of the obtaining conditions that will improve the similarity degree.

Figure 14:
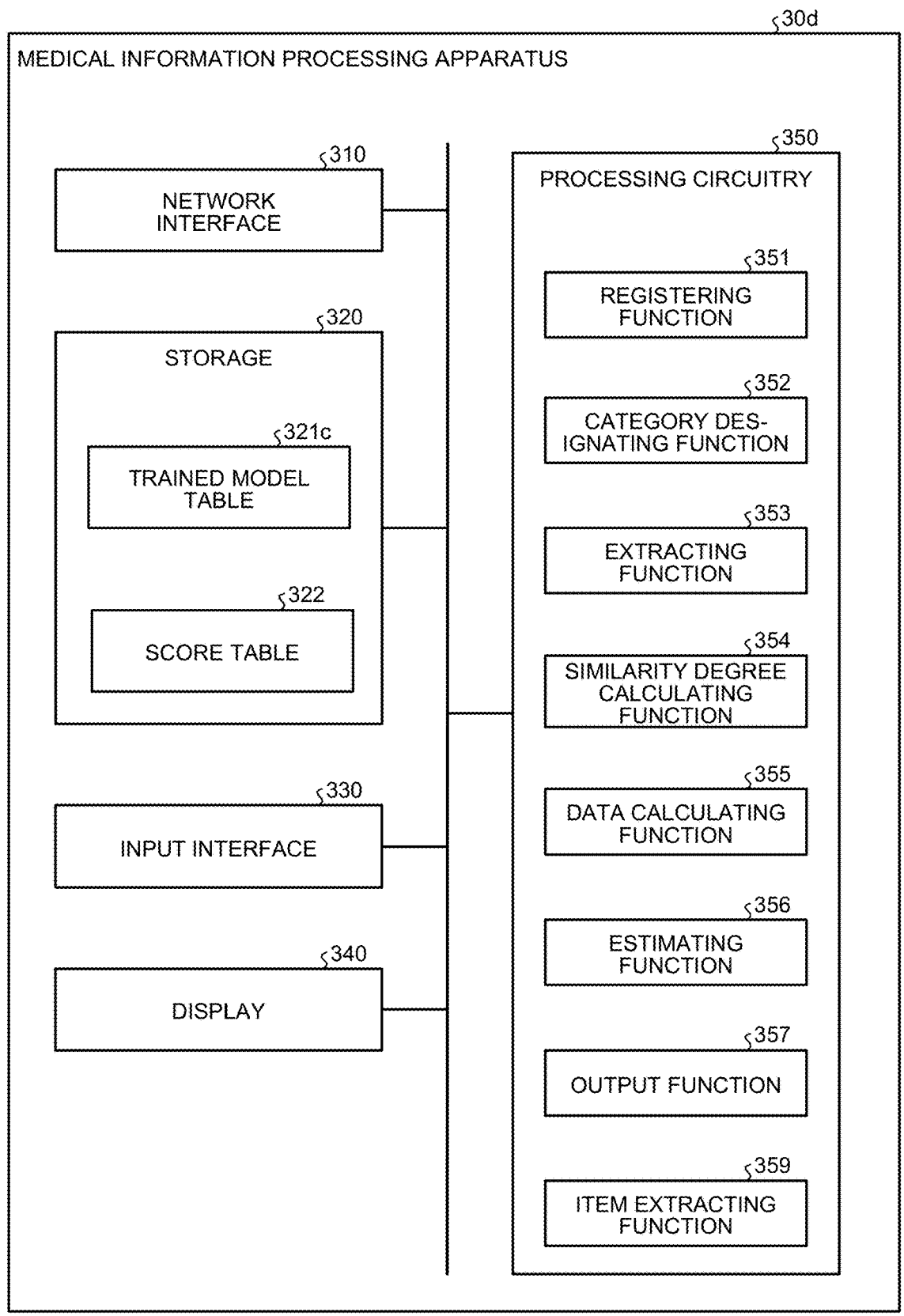
FIG. 14 is a block diagram illustrating an exemplary configuration of a medical information processing apparatus according to a fifth embodiment.

FIG. 14 is a block diagram illustrating an exemplary configuration of the medical information processing apparatus 30d according to the fifth embodiment.

Similarly to the third embodiment, a trained model table 321c keeps the following in correspondence with one another: trained models; the categories thereof; a plurality of training data sets; and obtaining conditions of the image data included in the training data sets. Further, similarly to the third embodiment, the storage 320 has the score table 322 stored therein.

Further, similarly to the third embodiment, on the basis of the score table 322, the similarity degree calculating function 354 is configured to extract the scores of the items of the obtaining conditions stored in the trained model table 321c and of the items of the obtaining conditions registered by the registering function 351. Further, the similarity degree calculating function 354 is configured to calculate the similarity degrees on the basis of the scores of the items.

Further, the medical information processing apparatus 30d includes an item extracting function 359. The item extracting function 359 is an example of a second extracting unit. The item extracting function 359 is configured to extract the item of the obtaining conditions that will improve the similarity degree between the first relevance information indicating the obtaining conditions of the image data used for generating the newly-generated trained model and the second relevance information indicating the obtaining conditions of the image data that was used for generating the existing trained model. More specifically, the item extracting function 359 is configured to extract an item having a lower score from among the items extracted by the similarity degree calculating function 354. When a score is increased, the precision level of the trained model will improve because the similarity degree improves. Accordingly, to improve the precision level, the item extracting function 359 is configured to extract at least one item having a lower score.

The output function 357 is configured to output the item of the obtaining conditions extracted by the item extracting function 359.

As explained above, the medical information processing apparatus 30d according to the fifth embodiment is configured to extract the item of the obtaining functions having a lower score, by comparing the obtaining conditions of the image data used for generating the newly-generated trained model, with the obtaining conditions of the image data that was used for generating the existing trained model. Further, the medical information processing apparatus 30d is configured to output the item having a lower score. Accordingly, the user is able to take measures to increase the score of the item of which the score is lower. Further, the medical information processing apparatus 30d may output a method for improving the score, with respect to the item of which the score is lower.

Further, in the embodiments above, the example was explained in which the medical information processing apparatus 30 has the characteristic functions; however, all or a part of the functions of the medical information processing apparatus 30, namely the registering functions 351, 351a, 351b, the category designating function 352, the extracting function 353, the similarity degree calculating functions 354, 354a, 354b, the data calculating function 355, the estimating function 356, the output function 357, the balance calculating function 358, and the item extracting function 359, may be included in the modality 10, may be included in the PACS 20, or may be included in an apparatus or a system other than the above.

In the embodiments escribed above, the example was explained in which the processing functions are realized by the single processing circuitry (i.e., the processing circuitry 350); however, possible embodiments are not limited to this example. For instance, the processing circuitry 350 may be structured by combining together a plurality of independent processors, so that the processing functions are realized as a result of the processors executing the programs. Further, the processing functions of the processing circuitry 350 may be realized as being distributed among, or being integrated together in, one or more processing circuits 350, as appropriate.

The term "processor" used in the explanations of the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in a memory, the programs may directly be incorporated in the circuits of one or more processors. In that situation, the one or more processors realize the functions by reading and executing the programs incorporated in the circuits thereof. Further, the processors of the present embodiments do not each necessarily have to be configured as a single circuit. It is also acceptable to structure one processor by combining together a plurality of independent circuits, so as to realize the functions thereof.

In this situation, the programs executed by the one or more processors are provided as being incorporated, in advance, in a Read Only Memory (ROM), a storage unit, or the like. Alternatively, the programs may be provided as being recorded in a computer-readable storage medium such as a Compact Disk Read-Only Memory (CD-ROM), a Flexible Disk (FD), a Compact Disk Recordable (CD-R), Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the functional units. In the actual hardware, as a result of a CPU reading and executing the programs from a storage medium such as a ROM, the modules are loaded into a main storage device and generated in the main storage device.

According to at least one aspect to the embodiments described above, it is possible to output the data quantity required in the re-learning process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
    processing circuitry configured to
        store, in an electronic memory, a first medical information training set that was used to generate a first trained machine-learning model, the first medical information training set including first medical image data obtained from scanning performed using a medical imaging apparatus, the first trained model being trained machine-learning to identify an object in the first medical image data;
        calculate, with respect to each second trained machine-learning model of a plurality of second trained machine-learning models being previously trained machine-learning models, a similarity degree between (1) a second medical information training set having been used in training the second trained machine-learning model, and (2) the first medical information training set, the second medical information training set including second medical image data obtained from scanning performed using the medical imaging apparatus, the second trained machine-learning model being trained to identify the object in the second medical image data;
        calculate, for each second trained machine-learning model of the plurality of second trained machine-learning models, a data quantity of the first medical information training set that causes, a precision of the second trained machine-learning model to achieve a target precision value by using data extracted from the electronic memory and indicating a correlational relationship between similarity degrees and corresponding data quantities that each achieves the target precision value when training is performed using image data having a corresponding similarity degree, wherein each second trained machine-learning model of the plurality of second trained machine-learning models can be retrained to become a new trained machine-learning model, based on the calculated similarity degree corresponding to the second trained machine-learning model;
        display, on a display device, a list of the calculated data quantity for each of the plurality of second trained machine-learning models;
        receive selection, by a user, of a particular one of the plurality of second trained machine-learning models displayed in the list of the calculated data quantity for each of the plurality of second trained machine-learning models; and
        in response to the selection by the user, re-train the particular one of the plurality of second trained machine-learning models selected by a the user to generate the new trained machine-learning model, using the corresponding calculated data quantity of the first medical information training set as training data.

2. The medical information processing apparatus according to claim 1, wherein the processing circuitry is further configured to
    estimate a correlational relationship between the data quantity and an accuracy rate of an output result from each of the plurality of second trained machine-learning models, and
    output information indicating the estimated correlational relationship.

3. The medical information processing apparatus according to claim 2, wherein the processing circuitry is further configured to
    calculate the data quantity based on the estimated correlational relationship, and
    output the calculated data quantity.

4. The medical information processing apparatus according to claim 1, wherein the processing circuitry is further configured to
    designate a category of the first trained machine-learning model in deep learning, from trained model information keeping the second trained machine-learning models, categories thereof, and the second medical information training set in correspondence with one another, extract one or more of the second trained machine-learning models that belong to the designated category, and calculate the similarity degree with respect to each of the one or more extracted second trained machine-learning models.

5. The medical information processing apparatus according to claim 4, wherein the processing circuitry is further configured to register the first medical information training set including first label data that is information identifying the first medical information, and designate the category based on the first label data.

6. The medical information processing apparatus according to claim 5, wherein the processing circuitry is further configured to calculate the similarity degree based on the first label data of the first medical information training set and second label data that is information identifying the second medical information training set.

7. The medical information processing apparatus according to claim 1, wherein the processing circuitry is further configured to calculate the similarity degree between the first medical information training set, which includes first image data for evaluating a capability of a first apparatus that generated the first image data used for generating the first trained machine-learning model and the second medical information training set, which includes second image data for evaluating a capability of a second apparatus that generated the second image data used for generating each of the second trained machine-learning models.

8. The medical information processing apparatus according to claim 1, wherein the processing circuitry is further configured to calculate the similarity degree between the first medical information training set, which includes a first obtaining condition of image data used for generating the first trained machine-learning model and the second medical information training set, which includes a second obtaining condition of image data that was used for generating each of the plurality of second trained, which includes models.

9. The medical information processing apparatus according to claim 1, wherein the processing circuitry is further configured to extract an item of obtaining conditions that improves the similarity degree between the first medical information training set indicating an obtaining condition of image data used for generating the first trained machine-learning model and the second medical information training set indicating an obtaining condition of image data that was used for generating each of the plurality of second trained machine-learning models, and output the extracted item.

* * * * *